United States Patent [19]  [11] 4,381,399
Olsen et al. [45] Apr. 26, 1983

[54] PURIFICATION OF TETRAHYDRODIBENZO[B,D]PYRANS FROM CRUDE SYNTHETIC MIXTURES

[75] Inventors: Robert E. Olsen, Placerville; Stephen J. Backlund, Fair Oaks, both of Calif.

[73] Assignee: Aerojet-General Corporation, LaJolla, Calif.

[21] Appl. No.: 332,644

[22] Filed: Dec. 21, 1981

[51] Int. Cl.³ .......................................... C07D 311/80
[52] U.S. Cl. .................................. 549/390; 210/635; 210/659
[58] Field of Search ...................... 260/345.3; 210/635, 210/659; 549/390

[56] References Cited

U.S. PATENT DOCUMENTS

| | | | |
|---|---|---|---|
| 3,560,528 | 2/1971 | Petrzilka | 260/345.3 |
| 3,668,224 | 6/1972 | Petrzilka | 260/345.3 |
| 3,833,616 | 9/1974 | Petrzilka | 260/345.3 |
| 3,920,705 | 11/1975 | Petrzilka | 260/345.3 |
| 4,116,979 | 9/1978 | Razdan et al. | 260/345.3 |

OTHER PUBLICATIONS

Fenimore et al., Analytical Chem., 45, 2331 (1973).
Monroe E. Wall, "The Chemistry and Metabolism of the Cannabinoids," The Interagency Committee on New Therapies for Pain and Discomfort, Report to the White House, U.S. Dept. of HEW, May 1979.
Mechoulam et al., "Recent Advances in the Chemistry and Biochemistry of Cannabis," Chemical Reviews, 76 (1), pp. 75–112 (1976).
Petrzilka et al., Helv. Chim. Acta., 52, 1102 (1969).
Razdan et al., J. Am. Chem. Soc., 96, 5860 (1974).

Primary Examiner—Nicky Chan
Attorney, Agent, or Firm—Townsend and Townsend

[57] ABSTRACT

(−)-6a,10a-Trans-1-hydroxy-3-n-pentyl-6,6,9-trimethyl-6a,7,8,10a-tetrahydrodibenzo[b,d]pyran or any of its related pyrans in which the n-pentyl group is replaced by hydrogen or $C_1$–$C_{10}$ alkyl is isolated from a crude synthetic mixture by a process which comprises esterifying the mixture to form perfluorinated alkanoic acid esters, removing low-boiling and non-volatile components, passing the mixture through a first gas chromatographic column with a packing whose liquid phase consists of a slightly polar phenyl-substituted silicone oil and recovering a fraction rich in the desired component, passing the recovered fraction through a second gas chromatographic column with a packing whose liquid phase consists of a non-phenyl-substituted silicone oil and recovering a fraction rich in the desired component, hydrolyzing the fraction recovered from the second stage, and recovering the desired product from the hydrolysis mixture.

16 Claims, No Drawings

PURIFICATION OF TETRAHYDRODIBENZO[B,D]PYRANS FROM CRUDE SYNTHETIC MIXTURES

Funding for the research to support this invention was supplied by the National Cancer Institute.

BACKGROUND OF THE INVENTION

The crude resin obtained from the flowering tops of female plants of several varieties of *Cannabis sativa* L. has been known for its psychotomimetic activity since antiquity. Common names assigned to some of these varieties include marijuana, hashish, charas, dagga, and bhang.

With the advent of advanced analytical techniques, it has been determined that the resin contains a variety of ingredients varying in molecular configuration, with both the components and their proportions varying from one source to the next. In general, the active compounds have the following formula where R is hydrogen or alkyl containing from one to ten carbon atoms. They are useful as psychotomimetic agents, sedatives, and analgesics.

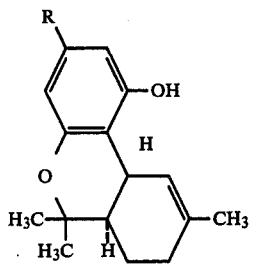

Extensive studies have led to the identification of a single component as the one primarily responsible for the psychotomimetic activity. Although its complicated ring structure gives rise to differing nomenclature depending upon the numbering system used, the active component is most commonly referred to as (−)-6a,10a-trans-1-hydroxy-3-n-pentyl-6,6,9-trimethyl-6a,7,8,10a-tetrahydrodibenzo[b,d]pyran, in which R in the formula above is n-pentyl and occupies the meta position with respect to the hydroxyl group. This components is also known by the simplified names "trans-$\Delta^9$-tetrahydrocannabinol" and "trans-$\Delta^9$-THC."

Following the identification of this ingredient, a variety of synthetic preparation methods were developed, in order to eliminate the need to extract the material from natural sources. A survey of these techniques can be found in the comprehensive article by Mechoulam et al., entitled "Recent Advances in the Chemistry and Biochemistry of Cannabis," *Chemical Reviews*, 76 (1), pp. 75-112 (1976). Two notable techniques are those described by Petrzilka et al. in *Helv. Chim. Acta*, 52, 1102 (1969), and by Razdan et al. in *J. Am. Chem. Soc.*, 96, 5860 (1974).

In addition to its psychotomimetic properties, the active ingredient has also been found to be a beneficial adjunct to cancer treatment in view of its ability to suppress the unpleasant side-effects which accompany chemotherapy. For this reason as well as its psychotomimetic activity, there is a serious need for comprehensive testing of the material in order to determine in full detail its pharmacological effects. For reliable and reproducible results, test samples of the material must be obtained in a highly pure state. Unfortunately, synthetic procedures tend to produce a mixture containing a broad variety of geometric isomers, optical isomers, intermediates, unreacted starting materials, and products of assorted side-reactions. Many of these can be separated from the active component by conventional separation techniques. A certain number, however, particularly the isomers, are extremely difficult to remove.

The only process developed to date which has been effective in supplying a product of sufficient purity is a low pressure liquid chromatography process. This process has several disadvantages. First, there are practical limitations on the scale-up of liquid chromotography equipment in terms of the diameter and length of the columns due to the need to avoid certain undesirable effects. Such limitations, together with considerations of packing efficiencies and absorbent weights, impose a severe limitation on the column through-put rate. As a result, a practical liquid chromatography system requires a tank farm containing several columns. Second, a solvent recovery system is necessary in order to separate out the product and recycle the solvent, entailing extensive processing equipment and the frequent attention of plant operators. This adds greatly to the expense. Third, the large number of vessels and transfer lines tends to increase the danger of handling losses and potential theft. A serious need thus exists for a simplified purification system with a lower capital investment, a lesser need for operator attention, a higher through-put rate, and better product accountability.

SUMMARY OF THE INVENTION

It has now been discovered that a compound of the above formula in which R is hydrogen or $C_1$–$C_{10}$ alkyl can be purified from a crude synthetic mixture by a relatively simple and highly efficient process which comprises (a) esterifying at least a portion of the mixture to form perfluorinated alkanoic acid esters, (b) removing low-boiling and non-volatile components, (c) passing the mixture through a first preparative gas chromatographic column containing a packing consisting essentially of a slightly polar phenyl-substituted silicone oil on a porous, inert, solid support to separate the mixture into a plurality of substantially discrete portions, and recovering therefrom the portion containing the highest proportion of the perfluorinated alkanoic acid ester of the desired component, or a substantial fraction of that portion, (d) passing the recovered portion or fraction through a second preparative gas chromatographic column containing a packing consisting essentially of a non-phenyl-substituted silicone oil on a porous, inert, solid support to further separate the portion or fraction into a plurality of substantially discrete subportions, and recovering therefrom the subportion containing the highest proportion of the perfluorinated alkanoic acid ester of the desired component, or a substantial subfraction of that subportion, (e) hydrolyzing the recovered subportion or subfraction to convert the esterified components back to their original form, and (f) recovering the desired component.

By virtue of its unique column staging arrangement, this process provides a composition of unusually high purity with an ease of operation and through-put capacity not heretofore seen in industrial scale attempts at preparing such materials. Whereas perfluorinated alkanoic acid esters are known in the art as a means of enhancing the volatility of the components for chromatographic purposes (see Mechoulam et al., ibid. at p. 93), the nature of the liquid phases described above and their use in this particular combination are novel and unique in their ability to separate the desired material from the other components in the mixture.

DESCRIPTION OF THE PREFERRED EMBODIMENTS

The process of the present invention is applicable to the preparation of purified forms of all compounds of the general formla in which R is hydrogen or alkyl containing from one to ten carbon atoms:

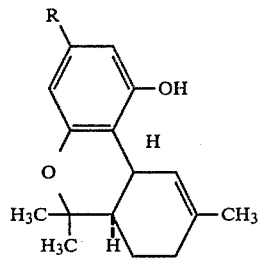

The term "alkyl" is used herein to designate both straight- and branched-chain alkyl groups within the stated range of carbon atoms. Examples include methyl, ethyl, n-propyl, isopropyl, n-butyl, t-butyl, n-pentyl, isopentyl, n-hexyl, n-octyl, and n-decyl. In one preferred embodiment of the formula, R occupies the meta-position on the ring relative to the hydroxyl group. Straight chains are particularly preferred, particularly those of two to eight carbon atoms in length.

The synthesis of (−)-6a,10a-trans-1-hydroxy-3-alkyl-6,6,9-trimethyl-6a,7,8,10a-tetrahydrodibenzo[b,d]pyrans, hereinafter referred to as "the trans-$\Delta^9$ isomer," can be accomplished in a variety of ways well documented in the literature. Most of the synthetic routes involve the reaction between a resorcinol (a 1,3-dihydroxy benzene) containing an alkyl substituent (or a hydrogen atom) corresponding to the R shown in the above formula (1,3-dihydroxy-5-n-pentylbenzene is known by the common name "olivetol") with a menthadienol or a closely related structural analog of the latter such as a menthadiene-ol or a menthenediol. An extensive list of synthetic routes is offered by Mechoulam et al., in "Recent Advances in the Chemistry and Biochemistry of Cannabis," Chem. Rev. 76 (1), 75-112 (1976). Each route produces a mixture of isomers, intermediates, unreacted starting material, and side-reaction products. Variations in the identity and proportion of the components in the product mixture occur from one route to the next. Many of the same impurities, however, are common to all synthetic routes. Any synthetic route, therefore, which produces the desired product indicated above is suitable for the present invention, and those which produce this material as a major component are preferred.

Particularly preferred processes are those involving the use of resorcinol or olivetol (or its alkyl analogs) and (+)-p-mentha-2,8-dien-1-ol. Notable in this regard are the processes developed by Petrzilka (U.S. Pat. Nos. 3,560,528, 3,668,224, 2,833,616, and 3,920,705) and Razdan et al. (U.S. Pat. No. 4,116,979). The disclosures of these patents are incorporated herein by reference. The most preferred process is that disclosed by Razdan et al. in the indicated patent, which offers a comprehensive description thereof.

This process basically involves reacting (+)-p-mentha-2,8-dien-1-ol with resorcinol or its alkyl-substituted analogs in the presence of a Lewis acid catalyst in an inert organic solvent under anhydrous conditions. The preferred Lewis acid is boron trifluoride etherate, and the anhydrous conditions are preferably maintained by the presence of a non-alkaline dehydrating agent such as magnesium sulfate.

The product mixture components are of low volatility and thus not conducive to vapor phase chromatographic separation. In order to convert them to a more volatile form, the mixture is esterified, whereby the hydroxyl groups are replaced by perfluorinated alkanoic acid ester moieties. Any perfluorinated alkanoic acid can be used, including straight- and branched-chain groups, with no critical limitation on the chain length. Straight chains are preferred, however, and chains of excessive length will be impractical since the volatility of the ester eventually begins to decrease as the chain continues to lengthen. Most conveniently, the ester moiety will contain from two to six carbon atoms. Examples include trifluoroacetate, pentafluoropropionate, heptafluorobutyrate, etc.

The esterifying agent itself can assume any conventional form, notably an acid anhydride, an acid halide, and an acyl imidazole, in addition to the acid itself. The acid itself is less preferred, since it has a greater tendency to isomerize the active trans-$\Delta^9$ component to the corresponding and less active trans-$\Delta^8$ isomer. The quantity of esterifying agent used is not critical. It is generally preferred, however, that an excess be used to insure a complete reaction. An excess in this context refers to the number of acyl moieties in the esterifying agent in comparison to the number of available hydroxyl groups in the product mixture. The amount of excess will most conveniently fall within the range of approximately fifty percent up to several thousand percent.

Although not essential, the esterification reaction is usually conducted in the presence of an inert organic solvent. It will be particularly convenient to use the same solvent used in the synthesis step. This eliminates the need to separate the products, isomers, intermediates, etc., from the solvent prior to treatment of the mixture with the esterifying agent. Useful solvents include conventional inert organic solvents such as aromatics, ethers, ketones, esters, and aliphatic hydrocarbons optionally chlorinated. Examples include petroleum ether, diethyl ether, benzene, toluene, tetrahydrofuran, dioxane, methylene chloride, chloroform, carbon tetrachloride, chlorobenzene, ethylene dichloride, and isopropyl ether. Chlorinated hydrocarbons are preferred.

The temperature of the esterification reaction is not limited to any critical range and can vary widely. For considerations of efficiency and optimal product recovery, however, elevated temperatures are less preferred, since high temperatures promote the isomerization of the trans-$\Delta^9$ isomer to its less active isomers (notably the trans-$\Delta^8$ isomer). Thus, the preferred temperature range is from about −20° C. to about +25° C., with about 0° C. to about 10° C. particularly preferred. Cooling can be accomplished by conventional externally applied cooling techniques, such as ice-water baths, dry ice-acetone baths, and cooling coils, and can be aided by appropriate agitation.

Once the esterification reaction is complete, or has been permitted to proceed to the desired degree, it will be beneficial to quench the reaction, since prolonged exposure to the acid produced as a by-product from the reaction will promote isomerization of the trans-$\Delta^9$ component to the trans-$\Delta^8$. Quenching can be accomplished by any conventional acid quenching agent, notably alkaline metal or alkaline earth metal carbonates or bicarbonates. Sodium or potassium bicarbonates are particularly useful in this regard. Again, this is not an essential feature of the process, but will be generally beneficial toward achieving the optimum yield of active ingredient.

Following the ester formation, high boiling and low boiling components are removed from the product mixture in order to provide efficient operation of the gas chromatographic columns and to prolong the useful life of the column packings. The low boilers include the solvent, any unreacted resorcinol and menthadienol (or whatever starting material is used), plus products of side-reactions involving the latter. The high boilers include impurities of high viscosity whose presence would impair the efficiency of the chromatographic columns.

With this in mind, any conventional separation method can be used. The preferred techniques are any of the various known forms of distillation. The primary concern in this portion of the process is the minimization of any opportunity for isomerization in the product mixture. Note that isomerization in this mixture, which occurs at increasing rates as the temperature rises, generally results in a decreasing proportion of the active trans-$\Delta^9$ isomer. Thus, short contact times and moderate operating temperatures are preferred. To achieve the most useful results, distillation under reduced pressure is preferred such that the operating temperature is maintained below about 250° C., with a practical operating range being from about 180° C. to about 220° C. To achieve this result, a column operating at a pressure of less than about 0.10 torr is preferred, with a pressure between about 0.005 and about 0.05 torr particularly preferred. A single stage distillation is generally sufficient although multiple stages can also be used. A particularly useful piece of equipment for this step is a wiped-film distillation apparatus.

Once the low-boiling components and non-volatiles have been removed, the product mixture is ready for the first stage of its separation by gas chromatography. The object of this stage as well as the second stage chromatographic separation is to divide the mixture into substantially discrete portions (or "peaks") which can be isolated from each other by a simple valve switching mechanism. The columns for each of the two stages are packed columns, the packing comprising particulate material consisting of an inert porous solid support wetted with an absorptive liquid phase.

The liquid phase in the first column consists of a silicone oil characterized by a slight polarity due to the presence of phenyl groups on the silicone molecule, and further characterized by the general absence of polar groups such as esters, cyano groups, trifluoromethyl groups, and ethers. Substituents other than phenyl groups can be present on the silicone backbone provided that they do not substantially alter the slightly polar character afforded by the phenyl groups. In addition, the phenyl groups themselves are optionally substituted with conventional substituents which are not highly polar, e.g., lower alkyl groups, halogens, etc., but preferably not nitro groups, cyano groups, trifluoromethyl groups, etc.

Any conventional support material can be used, provided that it is sufficiently porous to provide a high surface area for the liquid phase, and sufficiently inert that it does not promote decomposition of any of the components of the product mixture sought to be separated. A suitably inert support material will be essentially free of metal ions and acids, and will contain few or no acid sites. It is advisable that the support be silanized or otherwise passivated prior to being wetted with the liquid phase. Particularly suitable packing materials are calcined diatomite aggregates which have been acid washed and treated with dimethyldichlorosilane. Such materials are available from the Johns Manville Corporation under the trade name "Chromosorb ®."

The packing material as a whole is generally characterized by a maximum operating temperature, as a guide for preventin against loss of liquid phase by volatilization and against chemical degradation of the liquid phase. For the purposes of the present invention, there are no critical limits on the maximum operating temperature. It will be most convenient, however, to use a packing whose maximum operating temperature is 250° C. or greater.

The physical dimensions of the column itself are not critical and can vary over a wide range. They are generally limited by the range of equipment on the market as well as the desired through-put rate. Increased column lengths will generally promote more favorable "$\alpha$" values, where the $\alpha$ value for a given impurity peak is the ratio of the retention time for that peak to the retention time of the peak containing the desired trans-$\Delta^9$ component. Although no particular range of $\alpha$ values is critical, it will be most convenient to obtain a separation in which all $\alpha$ values differ from that of the desired peak by a minimum of 0.10. Different column lengths will provide varying degrees of peak resolution. Excessive lengths produce peak broadening, which detracts from a clean separation. The optimum column length can be selected with these considerations in mind. With a high degree peak of resolution and favorable retention times, injection batches can be overlapped in order to increase the through-put rate while still maintaining a clean separation of the desired peak. With these considerations in mind, it will be most convenient to use a column with a diameter of up to approximately 600 mm and a length ranging from approximately 0.5 to approximately 6.0 meters. Particularly preferred columns are those with a diameter ranging from approximately 20 to approximately 250 mm and a length ranging from approximately 1.0 to approximately 4.0 meters.

Any carrier gas can be used provided that it is inert and gaseous under the operating conditions of the column. The most useful carrier gases will be those with a high degree of dispersibility throughout the pores of the packing material. With this in mind, any conventional carrier gas used in either analytical or preparative gas chromatography can be used. This includes nitrogen, carbon dioxide, hydrogen, and helium, as well as other materials meeting the above description. In general, carrier gases with a low molecular weight are preferred, and helium is particularly preferred.

The flow rate of the carrier gas through the column, although not critical, should be fast enough to promote separation of the system components and to minimize the contact time and possible isomerization, yet slow enough to permit proper contact and permeability between the liquid and vapor phases and to prevent excessive pressure drop. Clearly, such features as peak resolution and broadening will be affected by the carrier gas flow rate. The flow rate will further depend on the column diameter, the density of the packing material, etc. Although no critical range exists, it will be most convenient to operate the column with a carrier gas flow rate of about 0.1 to about 2.0 liters per minute per square centimeter of column cross-section, preferably from about 0.2 to about 1.0 liters per minute per square centimeter.

The column temperature can also be varied widely with no critical range, although it is generally limited by the quoted maximum operating temperature of the packing material and by the desire to avoid isomerization of the trans-$\Delta^9$ isomer. Clearly, a shorter contact time will permit the use of a higher temperature in the column, since there will be less time for the product to convert to its isomers. With these considerations in mind, it will be most convenient to operate the column at a temperature within the range of approximately 100° C. to approximately 300° C., most preferably from about 150° C. to about 260° C. A constant and uniform temperature can be readily maintained by preheating the carrier gas to the same temperature as the column packing.

The product manifold at the exit of the column should be maintained at approximately the same temperature. The primary considerations here are to prevent condensation of the product components in the manifold and yet to avoid isomerization. The manifold will consist of an array of automatically operated valves directing the gases to any one of a series of condensers where the separated products are condensed out from the carrier gas. In order to determine the proper timing of the valves, the column exit line can be equipped with any conventional type of chromatograph detector to determine the retention times and magnitudes of the peaks. The most useful detectors are those which cause no physical or chemical change in the stream being measured, so that the entire exit stream can be routed through the detector. Thermal conductivity detectors are particularly useful in this regard. The detector will enable one to identify the elution times of any particular component as well as the shape and breadth of the peak containing this component. Once this information has been obtained, the collection manifold can be set up with a timer and automatic switching circuit to direct portions of the eluted material as desired to any of a series condensers arranged in parallel to provide individual fractions. When peak overlapping occurs on the product peak, recycling a portion of the peak can be beneficial in providing a higher purity product. The optimum portion of the peak for recycle and the amount of that portion will vary with the composition of the original mixture and are readily determined by routine experimentation. Condensation of the various components from the carrier gas can be achieved by any conventional condensation technique at any convenient temperature. Due to the high viscosity of the product materials, very low condensation temperatures are best avoided.

Once the desired peak or portion of the peak has been selected and isolated from the effluent of the first column and condensed out from the carrier gas, the resulting material is directed to the second stage of the gas chromatographic separation. The second column is similar to the first although it is characterized by a liquid phase consisting essentially of a silicone oil which is essentially non-phenyl-substituted. The oil will thus contain at most minor amounts of phenyl substituents sufficiently low in number that they have little or no effect on the behavior of the oil itself. In place of phenyl substituents, suitable oils will preferably have polar substituents. Examples include cyanoalkyl groups, fluorinated alkyl groups, etc. Particularly preferred are alkyl-substituted silicones where the alkyl groups have a minimum of three carbon atoms and are fully fluorinated from the third carbon outward. There is no critical upper limit on the length of the carbon chain, although as the chain length continues to increase, access of the carrier gas to the liquid phase will begin to diminish. With these considerations in mind, preferred alkyl groups are those with a chain length ranging from three to ten carbon atoms, with three to five carbon atoms particularly preferred. Examples of such alkyl groups are $-CH_2CH_2CF_3$, $-CH_2CH_2CF_2CF_3$, $-CH_2CH_2CF_2CF_2CF_3$, etc.

The column diameter and length, type of carrier gas, carrier gas flow rate, and operating temperature, are subject to the same considerations as those expressed above for the first stage. Considerations for the selection of product and recycle fractions are also the same, except that these two fractions will frequently be in the reverse order of that used for the first stage.

Product purity can be further enhanced by using multiple passes through each chromatographic separation stage.

It will be readily apparent to those skilled in the art that variations in the column packing material, the carrier gas, and the composition of the crude mixture will affect the optimum operating parameters such as the temperatures of the two columns, the carrier gas flow rate, the column lengths, the recycle portions and sizes, etc. Analytical scale columns containing the same packing material are highly useful for the screening of packing material candidates, since they offer a good approximation of the behavior of a preparative scale column with the same packing material. Analytical scale columns can be obtained from numerous suppliers, while preparative scale columns can be obtained from Elf Aquitaine Development, 9 West 57th Street, New York, New York 10019.

Once the final cut is obtained from the second stage of the chromatographic separation, it is hydrolyzed to convert the esterified components back to their original hydroxylated form. The result will be a composition of a high purity with regard to the trans-$\Delta^9$ isomer. Hydrolysis can be accomplished by any conventional technique. The variety of reagents and operating conditions which can be used are well within the knowledge of those skilled in the art. Typical reagents include alkali and alkaline earth metal hydroxides, preferably in aqueous solution. Examples are sodium, potassium, calcium and barium hydroxides, with sodium hydroxide particularly preferred. In view of its relatively low expense, together with the desirability of achieving a complete hydrolysis in a short amount of time, the hydrolyzing agent is preferably used in large excess, and the hydrolysis reaction is generally performed in the presence of a water immiscible solvent. This permits a convenient separation of the product from any unreacted caustic or other hydrolysis agent present as well as from the by-product alkanoic acid, thus enhancing the reaction rate. Suitable solvents include ethers, ketones, aromatics, hydrocarbons, and chlorinated hydrocarbons. The organic solvents recited above in connection with the esterification reaction are useful examples.

Once the hydrolysis has been completed, the product can be recovered from the solvent by any conventional recovery technique. Distillation will be particularly appropriate owing to the large difference in boiling points between the solvents and the product. As in all stages of the process, isomerization of the product and the consequent loss of its psychotomimetic properties can be minimized by avoiding the use of elevated temperatures. It should be noted, however, that the non-esterified material is more susceptible to isomerization than its esterified counterparts. Thus, preferred temperatures are those falling below about 150° C. The type of distillation apparatus which will accomplish this and the pressure under which the column operates will depend on the type of solvent used, and can be readily determined by routine experimentation.

The following examples are offered to illustrate the process of the present invention, and are intended neither to limit nor define the invention in any manner.

EXAMPLE 1

This example illustrates the preparation, purification, and recovery of (−)-6a,10a-trans-1-hydroxy-3-n-pentyl-6,6,9-trimethyl-6a,7,8,10a-tetrahydrodibenzo[b,d]pyran, hereinafter referred to as trans-$\Delta^9$-tetrahydrocannabinol or "trans-$\Delta^9$-THC," according to the process of the invention, using trifluoroacetyl esters.

A. Preparation of Synthetic Crude Mixture

A 12-liter flask maintained under a nitrogen atmosphere was charged with 8.0 liters of methylene chloride, 720 g (4.00 mol) of olivetol, 608 g (4.00 mol) of (+)-cis/trans-p-mentha-2,8-dien-1-ol, and 400 g (3.33 mol) of anhydrous magnesium sulfate. While the mixture was maintained at a temperature of 0°–5° C. by use of an ice-water bath, two portions of freshly distilled boron trifluoride etherate totaling 160 ml (1.28 mol) were added as follows: an initial 5-ml portion was added over a period of 10 minutes and an exotherm was observed up to 12° C., and the remainder was added approximately thirty minutes later when the reaction mixture had cooled back down to 5° C. The mixture was then stirred at 0°–5° C. until analysis by analytical gas chromatography indicated that the reaction was complete (about 3–4 hours). Then 800 g (9.25 mol) of solid sodium bicarbonate was added and the resulting mixture was stirred for thirty minutes at 0°–5° C. The solids were then filtered off and washed with 1.0 liter of methylene chloride.

B. Esterification

The solution from above was transferred to a 12 liter flask, cooled to 0°–5° C. in an ice-water bath, and treated with 1260 g (6.00 mol) of trifluoroacetic anhydride over thirty minutes. After stirring for 1 hour at 0°–5° C., the solution was siphoned over a thirty-minute period into a vigorously stirred mixture of 1600 g (16.0 mol) of potassium bicarbonate in 5 liters of water in a 5-gal (19-liter) glass bottle. This mixture was stirred vigorously for 1 hour at ambient temperature. The phases were then separated and the aqueous phase was washed with 1.0 liter of methylene chloride. The combined methylene chloride phases were washed with 1.0 liter of water and dried over 400 g of anhydrous magnesium sulfate. The magnesium sulfate was filtered off and the methylene chloride was removed under reduced pressure to give 1.6 kg of crude product of which about 40% was the desired trifluoroacetyl (hereinafter referred to as "TFA") derivative of $\Delta^9$-THC.

C. High- and Low-Boiler Removal

The crude TFA derivative was separated from volatile and non-volatile impurities by double distillation through a 17×2 cm Vigreaux column. The product distilled at 160°–170° C. (head temperature) and 0.3 Torr. The distillation data, with a rough analysis of the fraction collected in this temperature range obtained by analytical gas chromatography, is shown in Table 1.

TABLE 1.1

| Reduced Pressure Distillation of Crude TFA | | | |
|---|---|---|---|
| Distillation | Product Weight, kg | gc Assay, $\Delta^9$-TFA | Area Percent High-Boilers |
| 1 | 0.85 | 57.3 | 14.1 |
| 2 | 0.71 | 60.1 | 2.4 |

The balance of the distillate in each case consisted of isomers and other impurities with boiling points very close to that of $\Delta^9$-TFA. The final product fraction was a pale yellow liquid and was passed through the industrial scale chromatographic column without further treatment.

D. Chromatographic Separation-First Stage

The final TFA derivative of the preceding step was diluted with 0.14 kg of methylene chloride and the solution passed through a preparative gas chromatography column of the following specifications:

TABLE 1.2

| First Stage Column Specifications | |
|---|---|
| Diameter: | 40mm |
| Length: | 3.0m |
| Packing: | 10% (by weight) OV-17 ® (a phenylmethylsilicone of the general formula $[OSi(C_6H_5)(CH_3)]_n$ manufactured by Ohio Valley Specialty Co.) on Chromosorb ® W HP (a diatomite support manufactured by Johns-Manville Products Corp., Denver, Colorado) |
| Injector Temperature | 250° C. |
| Column Temperature | 245° C. |
| Detector (thermal conductivity) Temperature: | 245° C. |
| Collector Temperature: | 160° C. |
| Carrier Gas: | Helium at 7.5 l/min |
| Column Supplier: | Elf Aquitaine Development, 9 West 57th St., New York, N.Y. 10019 |

The eluting material was separated by collection manifold into four fractions and condensed with atmospheric steam. The third fraction was selected as the product fraction and the second was selected for recycle. Each of these fractions as well as the feedstock mixture was analyzed on a 25 meter by 0.3 mm capillary column of fused silica with a 5% phenyl/1% vinyl dimethylsilicone liquid phase designated as SE-54 ®, obtained from Hewlett-Packard Company, Palo Alto, Calif. (Model 5720A) with a flame ionization detector, to give the following composition:

TABLE 1.3

First Stage, First Pass Analysis by Capillary GC

| Stream | 1 | 2 | 3 | 4 | 5 | 6 | 7 | 8 | 9 | 10 |
|---|---|---|---|---|---|---|---|---|---|---|
| Feedstock | 15.9 | — | 2.2 | 43.1 | 0.5 | — | — | 6.6 | 0.4 | 0.5 |
| Product (Trap 3) | 2.9 | 0.3 | 2.8 | 66.9 | 0.8 | 0.2 | 0.4 | 13.4 | 1.1 | 1.1 |
| Recycle (Trap 2) | 26.0 | 0.3 | 3.5 | 56.3 | 1.2 | — | — | 5.1 | 0.2 | — |

From prior use of the same column on mixtures of known composition, the major peaks were identified as follows:

Peak 1: iso-THC and trans-$\Delta^8$-THC
Peak 3: cis-$\Delta^9$-THC
Peak 4: trans-$\Delta^9$-THC and abnormal-iso-THC
Peak 8: abnormal-THC The product (trap 3) fraction shown above was combined with corresponding product fractions from similar runs as well as product fractions from recycle passes, and then fed back through the same column for a second pass. The capillary column analysis gave the following results:

TABLE 1.4

First Stage, Second Pass Analysis by Capillary GC

| Stream | 1 | 2 | 3 | 4 | 5 | 6 | 7 | 8 | 9 | 10 |
|---|---|---|---|---|---|---|---|---|---|---|
| Feedstock | 7.3 | 0.9 | 5.1 | 69.2 | 1.8 | 0.5 | 0.2 | 9.6 | 1.0 | 1.4 |
| Product (Trap 3) | 0.4 | 0.4 | 1.9 | 71.1 | 0.4 | 0.8 | 0.6 | 15.2 | 2.4 | 2.9 |
| Trap 2 | 4.2 | 1.1 | 5.0 | 75.1 | 1.5 | 0.2 | 0.2 | 9.3 | 0.9 | 0.7 |

E. Chromatographic Separation—Second Stage

The product stream from the second pass above was passed through a second stage column of the following specifications:

TABLE 1.5

Second Stage Column Specifications

| | |
|---|---|
| Diameter: | 40mm |
| Length: | 2m |
| Packing: | 15% OV-202 ® (a trifluoropropylsilicone of the general formula [OSi(CH₃)(CH₂CH₂CF₃)]ₙ manufactured by Ohio Valley Specialty Co.,) on Chromosorb ® W HP |
| Injector Temperature | 225° C. |
| Column Temperature | 220° C. |
| Detector Temperature: | 220° C. |
| Collector Temperature: | 160° C. |
| Carrier Gas: | Helium at 7.5 l/min |
| Column Supplier: | Elf Aquitaine Development. |

Four fractions were again collected. This time, however, the second fraction (trap 2) was selected as the product fraction and the third (trap 3) was recycled. Analysis on the capillary column gave the following results:

TABLE 1.6

Second Stage, First Pass Analysis by Capillary GC

| Stream | 1 | 2 | 3 | 4 | 5 | 6 | 7 | 8 | 9 | 10 |
|---|---|---|---|---|---|---|---|---|---|---|
| Feedstock | 0.4 | 0.4 | 1.9 | 71.1 | 0.4 | 0.8 | 0.6 | 15.3 | 2.4 | 2.9 |
| Product (Trap 2) | 1.4 | 0.6 | 3.1 | 93.4 | — | 0.2 | — | 0.4 | — | 0.9 |
| Recycle (Trap 3) | 0.5 | 0.4 | 0.5 | 69.5 | 1.1 | 1.8 | 0.2 | 13.1 | 3.0 | 7.7 |

As with the first stage, the product fraction was combined with corresponding product fractions from similar runs and from recycle passes, and then fed back through the same column for a second pass to give the following results:

TABLE 1.7

Second Stage, Second Pass Analysis by Capillary GC

| Stream | 1 | 2 | 3 | 4 | 5 | 6 | 7 | 8 | 9 | 10 |
|---|---|---|---|---|---|---|---|---|---|---|
| Feedstock | 1.3 | 0.6 | 2.6 | 92.8 | — | 0.3 | — | 0.6 | 0.2 | 1.2 |
| Trap 2 | 2.0 | 0.6 | 3.0 | 93.8 | — | — | — | 2.0 | — | 0.2 |
| Trap 3 | 1.0 | 0.4 | 0.9 | 96.2 | — | — | — | 0.3 | — | 0.1 |

Each of the two fractions shown above indicate a high purity product. Attempts to do the same type of separation using different liquid phases outside the scope of the invention were not as successful. Liquid phases of the type used in this example are therefore unique.

F. Hydrolysis and Product Recovery

A 5.0 liter flask was charged with 3.0 liters of diethyl ether and 300 g (0.732 mol) of a product fraction obtained as described in the previous step. To this solution at ambient temperature was added 500 ml. (1.50 mol) of 3 M aqueous sodium hydroxide. This mixture was stirred vigorously for one hour at ambient temperature. The phases were then separated and the ether phase was washed with water (three 500 ml portions) until neutral. After drying over MgSO₄, the ether was removed by rotary evaporation. The trans-$\Delta^9$-THC was then distilled in two passes through a wiped-film still to remove any solvents and non-volatile impurities. The first pass was made at about 110° C. and 5–7 Torr to remove solvent and the second pass at about 200° C. and 0.5–1.0 Torr to distill the $\Delta^9$-THC.

EXAMPLE 2

This example illustrates the use of pentafluoropropionyl esters of the synthetic crude mixture in gas chromatographic separation. The esters were prepared and distilled in a manner analogous to that described in Example 1. Although analytical scale packed columns were used rather than preparative scale, the separations achieved give an accurate indication of the separation which will be achieved in a preparative scale unit.

The columns were as follows:
First stage: 10% OV-17 ® on Chromosorb ® W HP, length 10 feet (3.0 m), outer diameter ⅛ inch (3.2 mm), carrier gas helium at 28 ml/min, temperature 250° C.
Second stage: 5% An-600 ® (a cyanoethylmethylsilicone oil) on Chromosorb ® W HP, length 6 feet (1.8 m), outer diameter 2 mm, carrier gas helium at 20 ml/min, temperature 180° C.

The following table (Table 2.1) shows the retention times of the various peaks eluting from each of these columns expressed in terms of the "α value," where α is the ratio of the retention time of the peak (as measured from the solvent peak) to that of the peak corresponding to the trans-$\Delta^9$ component. The SE-54 ® capillary column of Example 1 is also included to show the composition of the crude mixture.

TABLE 2.1
Peak Retention Times for Pentafluoropropionyl Ester Mixture

| SE-54® Capillary | | OV-17® | | AN-600® | |
|---|---|---|---|---|---|
| α | Area % | α | Area % | α | Area % |
| .90 | 5 | .90 | 26 | .88 | 25 |
| .92 | 15 | — | — | — | — |
| .96 | 10 | — | — | — | — |
| 1.00 | 47 | 1.00 | 57 | 1.00 | 63 |
| 1.05 | 12 | — | — | 1.17 | 4 |
| 1.08 | 7 | 1.20 | 14 | 1.21 | 5 |
| 1.12 | 4 | 1.51 | 2 | 1.31 | 3 |

Since a peak separation satisfactory for preparative purposes is one where all impurity peaks are separated from the product peak by at least a 0.10 difference in α value, it is clear that the product peak in each case can be properly isolated.

EXAMPLE 3

This example illustrates the use of heptafluorobutyryl esters. The esters were prepared and distilled in a manner analogous to that described in Example 1. Using the same columns described in Example 2, the following results were obtained:

TABLE 3.1
Peak Reduction Times for Heptafluorobutyryl Ester Mixture

| SE-54® Capillary | | OV-17® | | AN-600® | |
|---|---|---|---|---|---|
| α | Area % | α | Area % | α | Area % |
| .91 | 10 | .90 | 43 | .88 | 43 |
| .93 | 32 | — | — | — | — |
| .96 | 4 | — | — | — | — |
| 1.00 | 45 | 1.00 | 50 | 1.00 | 53 |
| 1.13 | 5 | 1.05 | 6 | — | — |
| 1.28 | 1 | — | — | — | — |
| 1.31 | 3 | — | — | 1.45 | 4 |

Using the columns in sequence will clearly provide for adequate separation.

EXAMPLE 4

This example illustrates the collection and analysis of discrete fractions from packed columns using the same heptafluorobutyryl esters used in Example 3. Columns representing each of the two stages were used, each column measuring 10 feet (3.05 m) in length and ⅛ inch (0.32 cm) in outer diameter. Each column was equipped with a thermal conductivity detector in whose output line the eluting material condensed. Samples of the condensate were taken with a capillary-size collection tube over discrete periods of time designated as ranges of α-values. Each of these samples was then analyzed on the SE-54 capillary column used in the previous examples.

A. First Stage Column

A column with OV-17 packing was operated at 250° C. with helium as the carrier gas at a flow rate of 15 ml/min. Four fractions were collected, at α-value ranges of <0.88, 0.88–0.95, 0.96–1.02, and 1.04–1.10 (measured with respect to the trans-$\Delta^9$ peak). Capillary column analyses of each of these fractions are shown in Table 4.1. With this information plus the chromatogram trace from the thermal conductivity detector on the OV-17 column, α-values for each of the mixture components were determined. These are also shown in the table. All α values refer to the chromatogram trace from the OV-17 column, and all area percents refer to the chromatogram trace from the capillary column.

TABLE 4.1
Heptafluorobutyryl Ester Separation on OV-17

α ranges of fractions:
- Fraction A: <.88
- Fraction B: .88–.95
- Fraction C: .96–1.02
- Fraction D: 1.04–1.10

| Component | Area Percents by Capillary GC | | | | | α Value on OV-17 |
|---|---|---|---|---|---|---|
| | Feed | A | B | C | D | |
| abn-iso | 12 | 4 | 19 | 3 | 5 | >.88 |
| iso | 19 | 50 | 35 | — | 8 | <.88 |
| abn | 11 | 1 | — | — | 17 | 1.05 |
| cis-$\Delta^9$ | 2 | — | 2 | 8 | 5 | ~1.0 |
| trans-$\Delta^8$ | 12 | 37 | 35 | 3 | 9 | .88 |
| trans-$\Delta^9$ | 31 | 4 | 3 | 82 | 50 | 1.0 |
| dimers | 6 | — | — | — | — | >1.3 |
| dimers | 6 | — | — | — | — | >1.3 |

It is clear from the above that all components except the abnormal and cis-$\Delta^9$ isomers are adequately separated (by "adequate separation" is intended a separation with an α value removed from the product peak by approximately 0.10 or greater). The following section demonstrates that these two isomers are readily separated in the second stage.

B. Second Stage Column

A column with OV-210 packing (a 10% trifluoropropylsilicone on Chromosorb W HP) was operated at 225° C. with helium as the carrier gas at a flow rate of 20 ml/min. Three fractions were collected and analyzed on the capillary column, and α values were determined as in the first stage. The results are shown in Table 4.2.

TABLE 4.2
Heptafluorobutyryl Ester Separation on OV-210

α Ranges of Fractions:
- Fraction A: .87–.92
- Fraction B: .99–1.01
- Fraction C: 1.05–1.30

| Component | Area Percents by Capillary GC | | | | α Value on OV-210 |
|---|---|---|---|---|---|
| | Feed | A | B | C | |
| abn-iso | 11 | — | 2 | 77 | 1.2 |
| iso | 18 | 46 | — | 6 | .88 |
| abn | 10 | — | 3 | — | 1.4 |
| cis-$\Delta^9$ | 1 | 4 | — | — | ~.9 |
| trans-$\Delta^8$ | 13 | 7 | — | 4 | .91 |
| trans-$\Delta^9$ | 35 | 40 | 89 | 9 | 1.0 |

It is clear from this table that isomers which are not adequately separated from the trans-$\Delta^9$ peak in the first stage will be adequately separated on this column.

To further show the efficacy of this type of liquid phase in the second stage column packing, an additional liquid phase outside the scope of the present invention was used. This material is designated OV-225, and is a phenylcyanopropylsilicone of the general formula [OSi(C$_6$H$_5$)(CH$_3$)]$_n$[OSi(CH$_3$)(CH$_2$CH$_2$CH$_2$CN)]$_n$ on Chromosorb W AW support (10% by weight). The latter is another diatomite support similar to Chromosorb W HP. The operating conditions were otherwise identical to those used on the OV-210, except that four fractions were taken rather than three. The results are shown in Table 4.3.

TABLE 4.3

| Heptafluorobutyryl Ester Separation on OV-225 | | | | | | |
|---|---|---|---|---|---|---|
| α ranges of fractions: | | | | | | |
| Fraction A: | | | | .84–.90 | | |
| Fraction B: | | | | .99–1.01 | | |
| Fraction C: | | | | 1.04–1.08 | | |
| Fraction D: | | | | 1.10–1.30 | | |
| | Area Percents by Capillary GC | | | | | α Value on |
| Component | Feed | A | B | C | D | OV-225 |
| abn-iso | 11 | — | — | 80 | 4 | 1.06 |
| iso | 18 | 55 | — | 1 | — | .86 |
| abn | 10 | — | 3 | — | 89 | 1.22 |
| cis-Δ⁹ | 1 | 1 | — | — | — | <1.00 |
| trans-Δ⁸ | 13 | 39 | — | — | — | .86 |
| trans-Δ⁹ | 35 | 4 | 87 | 3 | 2 | 1.00 |

Clearly, the separation of cis-$\Delta^9$ isomer from the product peak is inadequate. It is also clear that the separations of both the abn and abn-iso peaks from the product peak are inferior. The trifluoropropyl silicone is clearly a superior liquid phase for the second stage.

We claim:

1. A process for the isolation of a compound of the formula:

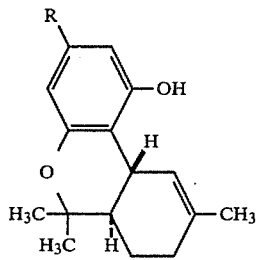

in which R is hydrogen or $C_1$-$C_{10}$ alkyl from a crude synthetic mixture, comprising the steps of:
 (a) esterifying at least a portion of the components of said mixture to form perfluorinated alkanoic acid esters thereof,
 (b) removing low-boiling components and non-volatile components from said mixture,
 (c) passing said mixture through a first preparative gas chromatographic column containing a packing consisting essentially of a slightly polar phenyl-substituted silicone oil on a porous, inert solid support to separate said mixture into a plurality of substantially discrete portions, and recovering therefrom the portion containing the highest proportion of the perfluorinated alkanoic acid ester of said compound, or a substantial fraction of said portion,
 (d) passing said recovered portion or fraction through a second preparative gas chromatographic column containing a packing consisting essentially of a non-phenyl-substituted silicone oil on a porous, inert solid support to further separate said portion or fraction into a plurality of substantially discrete subportions, and recovering therefrom the subportion containing the highest proportion of the perfluorinated alkanoic acid ester of said compound, or a substantial subfraction of said subportion,
 (e) hydrolyzing said recovered subportion or subfraction to convert the perfluorinated alkanoic ester moieties contained therein to hydroxyl groups, and
 (f) recovering said compound from said hydrolyzed subportion or subfraction.

2. A process according to claim 1 in which R is $C_1$-$C_{10}$ alkyl.

3. A process according to claim 1 in which R is n-pentyl.

4. A process according to claim 1, 2, or 3 in which the crude synthetic mixture is obtained by reacting an appropriately substituted resorcinol with (±)-p-mentha-2,8-dien-1-ol in the presence of a catalytic amount of a Lewis acid catalyst and an excess of a non-alkaline dehydrating agent, at a temperature of from about −20° C. to about +25° C.

5. A process according to claim 1, 2, or 3 in which the crude synthetic mixture is obtained by reacting 5-n-pentyl-resorcinol with (+)-p-mentha-2,8-dien-1-ol in the presence of a catalytic amount of boron trifluoride etherate and an excess of anhydrous magnesium sulfate, at a temperature of from about −5° C. to about +5° C., in the presence of an inert chlorinated hydrocarbon solvent.

6. A process according to claim 1, 2, or 3 in which step (a) is accomplished by treating the crude synthetic mixture with an excess of a member selected from the group consisting of an acid anhydride, an acid halide, and an acyl imidazole of a perfluorinated alkanoic acid of from 2 to 6 carbon atoms, at a temperature of from about −20° C. to about +25° C.

7. A process according to claim 1, 2, or 3 in which step (a) is accomplished by treating the crude synthetic mixture with at least a 50% excess of trifluoroacetic acid anhydride at a temperature of from about 0° C. to about 10° C. in the presence of an inert chlorinated hydrocarbon solvent.

8. A process according to claim 1, 2, or 3 in which step (b) is accomplished by distilling said mixture at a temperature below about 250° C. and a pressure below about 0.1 Torr.

9. A process according to claim 1, 2, or 3 in which step (b) is accomplished by distilling said mixture at a temperature of from about 180° C. to about 220° C. and a pressure of from about 0.005 to about 0.05 Torr.

10. A process according to claim 1, 2, or 3 in which the packing of step (c) consists essentially of a phenylmethylsilicone on an acid-washed silanized diatomite support, and occupies a space with a diameter of up to about 600 mm and a height of from about 0.5 m to about 6.0 m, and the column is operated at a temperature of from about 100° C. to about 300° C. with a carrier gas flow rate of from about 0.1 to about 2.0 liters per minute per square centimeter of column cross-section.

11. A process according to claim 1, 2 or 3 in which the packing of step (c) consists essentially of a phenylmethylsilicone on an acid-washed silanized diatomite support, and occupies a space with a diameter of from about 20 mm to about 250 mm and a height of from about 1.0 m to about 4.0 m, and the column is operated at a temperature of from about 150° C. to about 260° C. with a carrier gas flow rate of from about 0.2 to about 1.0 liters per minute per square centimeter of column cross-section, and with a carrier gas selected from the group consisting of nitrogen, carbon dioxide, hydrogen, and helium.

12. A process according to claim 1, 2, or 3 in which the packing of step (d) consists essentially of a member selected from the group consisting of cyanoalkyl silicones and fluorinated alkyl silicones on an acid-washed silanized diatomite support, and occupies a space with a diameter of up to about 600 mm and a height of from about 0.5 m to about 6.0 m, and the column is operated at a temperature of from about 100° C. to about 300° C. with a carrier gas flow rate of from about 0.1 to about 2.0 liters per minute per square centimeter of column cross-section.

13. A process according to claim 1, 2, or 3 in which the packing of step (d) consists essentially of $C_3$–$C_{10}$ alkyl substituted silicones in which the alkyl groups are fully fluorinated from the third carbon outward, on an acid-washed silanized diatomite support, and said packing occupies a space with a diameter of from about 20 mm to about 250 mm and a height of from about 1.0 m to about 4.0 m, and the column is operated at a temperature of from about 150° C. to about 230° C. with a carrier gas flow rate of from about 0.2 to about 1.0 liters per minute per square centimeter of column cross-section, and a carrier gas selected from the group consisting of nitrogen, carbon dioxide, hydrogen, and helium.

14. A process according to claim 1, 2, or 3 in which the packing of step (c) consists essentially of a phenylmethylsilicone on an acid-washed silanized diatomite support, and occupies a space with a diameter of from about 20 mm to about 250 mm and a height of from about 2.0 m to about 4.0 m, and the column is operated at a temperature of from about 150° C. to about 260° C., with helium as the carrier gas at a flow rate of from about 0.2 to about 1.0 liters per minute per square centimeter of column cross-section; and the packing of step (d) consists essentially of a methyl-3,3,3-trifluoropropylsilicone on an acid-washed silanized diatomite support, and occupies a space with a diameter of from about 20 mm to about 250 mm and a height of from about 1.0 m to about 4.0 m, and the column is operated at a temperature of from about 150° C. to about 230° C., with helium as the carrier gas at a flow rate of from about 0.2 to about 1.0 liters per minute per square centimeter of column cross-section.

15. A process according to claim 1, 2, or 3 in which step (e) accomplished by treating said recovered subportion or subfraction with an aqueous solution of an alkali or alkaline earth metal hydroxide in the presence of a water-immiscible solvent.

16. A process according to claim 1, 2, or 3 in which step (e) is accomplished by treating said recovered subportion or subfraction with an excess of an aqueous solution of sodium hydroxide in the presence of diethyl ether.

* * * * *